(12) United States Patent
Santos et al.

(10) Patent No.: US 9,115,106 B2
(45) Date of Patent: Aug. 25, 2015

(54) USE OF 5-HYDROXY-2-HYDROXYMETHYL-γ-PYRONE (HMP) AS A LEISHMANICIDAL AGENT

(75) Inventors: Alberdan Silva Santos, Belem (BR); Edilene Oliveira da Silva, Belem (BR); Jose Luiz Martins do Nascimento, Belem (BR); Claudio Naum Alves, Ananindeua (BR); Ana Paula Drumond Rodrigues, Belem (BR); Antonio Sergio da Costa Carvalho, Marituba (BR)

(73) Assignee: UNIVERSIDADE FEDERAL DO PARA (BR)

( * ) Notice: Subject to any disclaimer, the term of this patent is extended or adjusted under 35 U.S.C. 154(b) by 648 days.

(21) Appl. No.: 13/058,899

(22) PCT Filed: Aug. 14, 2009

(86) PCT No.: PCT/BR2009/000254
§ 371 (c)(1),
(2), (4) Date: Mar. 31, 2011

(87) PCT Pub. No.: WO2010/017613
PCT Pub. Date: Feb. 18, 2010

(65) Prior Publication Data
US 2011/0178169 A1   Jul. 21, 2011

(30) Foreign Application Priority Data
Aug. 14, 2008   (BR) .................... 000185/08

(51) Int. Cl.
*A01N 43/16* (2006.01)
*A61K 31/35* (2006.01)
*C07D 315/00* (2006.01)
*A61K 31/366* (2006.01)
*A61K 31/351* (2006.01)
*C07D 309/40* (2006.01)

(52) U.S. Cl.
CPC ............ *C07D 309/40* (2013.01); *A61K 31/351* (2013.01); *A61K 31/366* (2013.01)

(58) Field of Classification Search
USPC .......................................... 514/460; 549/417
See application file for complete search history.

(56) References Cited

U.S. PATENT DOCUMENTS 5,164,182 A * 11/1992 Meybeck et al. ............. 424/773

FOREIGN PATENT DOCUMENTS

| WO | 2006037958 A2 | 4/2006 |
| WO | 2006037958 A3 | 4/2006 |

OTHER PUBLICATIONS

Posakony et. al., Journal of Medicinal Chemistry, 2004, American Chemical Society, vol. 47, pp. 2635-2644.*
Xiong et. al., Bioorganic and Medicinal Chemistry, 2001, Pergamon, vol. 9, pp. 1773-1780.*
Clarkson et. al., Molecular and Biochemical Parasitology, 1981, Elsevier, vol. 3, pp. 271-291.*
International Search Report and Written Opinion dated Jan. 25, 2010.
Kayser, et al., Antileishmanial Activity of Two Gamma-Pyrones from Podolepsis Hieracioides (Asteraceae), Acta Tropica, Apr. 2003, vol. 86, Nr. 1, pp. 105-107.
de Fatima, et al., "Trypanocidal Activity of 5,6-dihydropyran-2-ones against Free Trypomastigotes Forms of Trypanosoma Cruzi" European Journal of Medicial Chemistry, Oct 2006, vol. 41, Nr. 10, pp. 1210-1213.
Dobias J.; "Effect of Kojic Acid Phenylosazone on Trypanosoma Cruzi"; Institute of Molecular Biology, Bratislava, Czechoslovakia; 35, 3, 203-207; 1980; 5 pages.

* cited by examiner

*Primary Examiner* — Sarah Pihonak
(74) *Attorney, Agent, or Firm* — Thomas Horstemeyer, LLP

(57) ABSTRACT

The present invention refers to the use of HMP (a secondary metabolite obtained from *Aspergillus* fungi) as an agent that intensifies the mechanism of macrophage activation, leading to the death of *L. (Leishmania) amazonensis*, the etiologic agent of cutaneous leishmaniasis. The main mechanism of action of this agent is the activation of the microbicidal activity of host cells, through increased superoxide production, number of lysosomes, actin and microtubule filament polymerization and increased spreading, typical of activated cells. Additionally, HMP represents a molecule of easy acquisition, presents an efficient combat mechanism with no adverse reactions and capacity to inhibit the development of promastigotes and amastigotes forms. Finally, results suggest HMP to be a potential candidate for use against cutaneous leishmaniasis at a minimal concentration of 50 μg/mL.

6 Claims, No Drawings

USE OF 5-HYDROXY-2-HYDROXYMETHYL-γ-PYRONE (HMP) AS A LEISHMANICIDAL AGENT

CROSS REFERENCE TO RELATED APPLICATION

This application is the 35 U.S.C. §371 national stage of, and claims priority to, PCT application PCT/BR2009/000254, filed Aug. 14, 2009 claiming priority of Brazilian Patent Application No. 000185/08 filed on Aug. 14, 2008, the disclosure of which is hereby incorporated by reference.

FIELD OF THE INVENTION

This application refers to the use of 5-hydroxy-2-hydroxymethyl-γ-pyrone (HMP) as a leishmanicidal agent by activation of the host cell, which blocks the proliferation of the protozoan, *Leishmania (Leishmania) amazonensis*, etiologic agent of cutaneous leishmaniasis (CL). In vitro studies, performed with HMP on infected macrophages, showed that its mechanism of action is based on the stimulation of oxygen radical production, which in turn increases the amount of lysosomes, the cytoskeleton polymerization (actin filaments and microtubules), and causes spreading of the host cell. These alterations characterize a state of activation of these cells and the consequent elimination of the agent of infection. Thus, action on the host cell and protozoan was observed, for the first time in our laboratories, using HMP in experimental methods described here. It should be emphasized that there are no reports in the literature regarding these procedures.

BACKGROUND OF THE INVENTION

Leishmaniasis is a neglected tropical disease that affects about 2 million people worldwide, being one of the six tropical diseases of major global importance. According to the World Health Organization, leishmaniasis affects 88 countries, among which 72 are classified as developing countries (WHO: The Special Program for Research and Training in Tropical Diseases. Leishmaniasis: disease information. Available at http://www.who.int/tdr/diseases/leish/diseaseinfo.htm. Last access on: Apr. 4, 2009).

In the Americas, 11 (eleven) dermotropic species of *Leishmania* are currently known to cause human disease and 8 (eight) species have been described in animals. In Brazil, 7 (seven) species have been identified; from which 6 (six) belong to the *Viannia* or *Leishmania* subgenera. The best known species are: *Leishmania (Viannia) braziliensis, L. (V.) guyanesis* and *L. (Leishmania) amazonensis*. In Brazil, during the 1980's, an increase in registered cases was observed, with 3,000 cases being recorded in 1980 rising to 37,710 cases in 2001. Data indicate that the Northern region of the country has a density of 552 cases per 10,000 inhabitants, especially in the great region of Tucurui, which encompasses the states of Pará, Maranhão and Tocantins (Ministério da Saúde, Departamento de Vigilância da Saúde. Manual de Vigilância da Leishmaniose Tegumentar Americana. Série A. Normas e Manuais Técnicos. Editora M S, 2ª ed., Brasília, 2007).

The first choice of drugs for the treatment of CL is pentavalent antimonials, described by the U.S. Pat. No. 1,984,480, 1934, have been used since 1945 and are administered intraperitoneally; however these agents have collateral effects such as myalgia, nausea, vomiting, abdominal pain and fever. The treatment of second choice consists of intramuscular injections of pentamidine and intravenous injections of amphotericin, as described in U.S. Pat. No. 2,908,611, 1959; however both have also shown adverse effects, such as nausea, pain at the injection site, cardiorespiratory symptoms, fever and anemia (Lima, E. B.; Porto, C.; Mota, J. O. C.; Sampaio, R. N. R.; Tratamento da Leishmaniose Tegumentar Americana *Anais Brasileiros de Dermatologia*. 82(2), 111, 2007; Amato, V. S.; Tuon, F. F.; Bacha H. A. Neto, V. A.; Nicodemo, A. C.; Review—Mucosal leishmaniosis Current Scenario and Prospects for Treatment *Acta Tropica* 105, 1, 2008).

Other drugs are also used in the control of cutaneous leishmaniasis, including the amino glycoside antibiotic paromomycin, described in patent EP0435915, 1993; It has been administered by the parenteral route since the 1960's, and is combined with salts, urea or gentamicin in appropriate concentrations, in accordance with the intruder species. However, the use of paromomycin via new routes of administration has been developed, as the in emulsion formulation for topical use (see U.S. Pat. No. 6,284,739, 2001). This drug acts primarily by altering the membrane properties of *Leishmania* and inhibiting macromolecular synthesis (Misha, J.; Saxena, A; Singh, S.; Chemotherapy of Leishmaniasis: Past, Present and Future *Curr Med Chem* 5, 312, 2007).

The drug miltefosine, described by the patent EP1051159, 2002 is another medicinal product that is being widely studied as the first oral treatment effective in combating visceral leishmaniasis. This drug is at stage VI of tests in humans in India. Amphotericin B has also been subjected to a series of studies aiming at reducing the adverse effects through the use of liposome containing amphotericin (see U.S. Pat. No. 5,965,156, 1999).

In addition to synthetic drugs, there are other natural substances that have demonstrated great therapeutic and leishmanicidal potential; such substances include alkaloids, terpenoids, flavonoids, steroids, among others, from more than 101 plants found, mainly in Bolivia, Colombia, Brazil, Venezuela and India (Rocha, L. G.; Almeida, J. R. G. S.; Macedo, R. O.; Barbosa-Filho, J. M.; A review of Natural Products With Antileishmanial Activity *Phytomedicine* 12, 514, 2005); however, substances isolated from plants have low concentrations of its active ingredients, and it should be taken into account the factor of seasonality that, in many cases, limits the continued production of these metabolites on a commercial scale.

In Brazil, the treatment of leishmaniasis complies with the standards established by the World Health Organization (WHO), which recommend the use of pentavalent antimonials as the first choice in treatment, followed by amphotericin B and pentamidine. Some natural substances have also been subject of research in Brazil to combat cutaneous leishmaniasis. These include essential oils rich in linalool or eugenol from plants of the *Croton cajucara* and *Ocimum gratissimu* species, respectively (Rosa, M. S. S.; Mendonca-Filho, R. R.; Bizzo, H. R.; Rodrigues, I. A.; Soares, R. M.; Souto-Padron, T.; Alviano, C. S.; Lopes, A. H.; Antileishmanial Activity of a Linalool-Rich Essential Oil from *Croton cajucara*. *Antimicrobial Agents and Chemotherapy* 47, 1895, 2003). In addition to the essential oils, alkaloids from species *A. crassiflora, A. coriacea, G. australis* and *C. ovalifolia* are also being studied (Tempone, A. G.; Borborema, S. E. T.; Andrade Jr., H. F.; Gualda, N. C. A.; Togi, A.; Carvalho, C. S.; Bachiega, D.; Lupo, F. N.; Bonoto S. V.; Fisher, D. C. H.; Antiprotozoal Activity of Brazilian Plant Extracts from Isoquinoline Alkaloid-Producing Families. *Phytomedicine* 12, 382, 2005). Hydroalcoholic extracts from the *Stachytarpheta cayennensis* plant species have been used for the treatment of CL (Moreira, R. C. R.; Costa, G. C.; Lopes, T. C.; Bezerra, J. L.;

Guerra, R. N. M.; Rebêlo, J. M. M.; Ribeiro, M. N. S, Nascimento, F. R. F.; Costa, J. M. L.; In vitro leishmanicidal effect of *Stachytarpheta cayennensis* (Rich.) Vahl (Verbenaceae), *Rev. Bras. Farmacogn* 17, 59, 2007), as well as the ethanolic extract from propolis, which has demonstrated effectiveness through the activation of the host cell (Ayress, D. C.; Marcucci, M. C.; Giorgio, S.; Effects of Brazilian própolis on *Leishmania amazonensis Mem Inst Oswaldo Cruz.* 102(2), 215, 2007).

Another natural product that has been widely studied is a homeopathic medicine named Canova, which has microbicidal activity in host cells such as macrophages. This substance was developed in Argentina and it is currently commercialized in Brazil. (Pereira, W. K. and co-workers; Immunomodulatory effect of Canova medication on experimental *Leishmania amazonensis* infection. *Journal of Infection* 51, 157, 2005; Oliveira, C. C., Oliveira, S. M., Godoy, L. M. F.; Gabardo, J.; Buchi, D. F.; Canova, a Brazilian medical formulation, alters oxidative metabolism of mice macrophages *Journal of Infection* 52, 420, 2006), however this product is prepared as a compound in which five plant species are used for their production, limiting a large scale production.

The search for leishmanicidal agents has been a major challenge during recent years, particularly because this disease is considered to be negligible and also has little economic appeal. As such, the search continues for molecules that can be easily obtained, do not depend on seasonality and do not have any limitation to their production. New drugs should also provide an efficient mechanism to eliminate the *Leishmania* inside the host cell without causing adverse reactions, enabling a large scale production with commercial prospects. In this context, the secondary metabolite produced by biotechnological processes from filamentous fungi, such as HMP, has all these characteristics and is a potential candidate for the combat of cutaneous leishmaniasis.

HMP was discovered in 1907. This secondary metabolite was used, initially, as dietetic, antioxidant, dye, and later as a preservative. Currently, besides being widely used as an additive in food it is also used in cosmetics as a skin bleaching agent. It is also widely used in medicine as an anti-inflammatory drug and the study of its derivatives has been directed towards other biological tests of socio-economic interest.

Based on the literature reviewed and discussed in a paper by Burdock et al. (Burdock, G. A.; Soni, M. G.; Cabin, I. G. Evaluation of health aspects of HMP in food. *Regulatory and Pharmacology* 33, 80, 2001), the consumption of levels of HMP usually found in foods does not present a concern for safety in human health. This conclusion was also drawn by Nohyneka and co-workers in his studies of the genotoxic action of HMP (Nohyneka, G. J; Kirkland, D.; Marzin, D.; Toutain, H.; Leclerc-Ribaud, C.; Kinnai, H.; assessment of the genotoxicity and human health risk of topical use of HMP [5-hydroxy-2-(hydroxymethyl)-4H-pyran-4-one] *Food and Chemical Toxicology* 42, 93, 2004).

This substance is a metabolite that is usually produced by many species of fungi and bacteria belonging to the genera *Aspergillus, Acetobacter* and *Penicillium* (Burdock, G. A.; Soni, M. G.; Cabin, I. G.; Evaluation of health aspects of kojic acid in food. *Regulatory and Pharmacology* 33, 80, 2001). Tolentino (Tolentino, L. A. A Reinvestigation of the Chemistry of Kojic Acid. II, The Synthesis and Isomerization of alpha-Methyl and Gamma-Methylglutaconic Acids. UMI Dissertation Services, Ann Arbor, Mich. 1974) reported on the structure and chemistry of HMP (recorded as CAS No. 501-30-4) providing the empirical formula, $C_6H_6O_4$, and a molecular weight of 142.109 g·mol$^{-1}$. This molecule crystallizes as prismatic needles in acetone, ethanol and ether or methanol and ethyl acetate. Its melting point is around 153-154° C. and it presents an estimated pKa of 7.90 and 8.03. HMP is freely soluble in water, ethanol, or acetone. During the process for obtaining HMP, after completion of fermentation, it can be recovered by one of the following physical and chemical methods: (1) precipitation as cuprum salt, (2) extraction with ethyl acetate, (3) continuous extraction with ether, (4) evaporation to a small volume which leads to crystallization or crystallization at 0° C., (5) extraction with chloroform, or (6) adsorption on active carbon followed by elution with butyl acetate saturated with ammonia (Bajpai, P.; Agrawala, D. K.; Vishwathan, L.; Kojic acid: synthesis and properties. *J. Sci. Ind. Res.* 41, 185, 1982).

From the information obtained in the literature, no incidents of poisoning in humans by HMP were observed. There are also no data in the literature describing the process of excretion of HMP by the human body. However, due to its structure, this substance probably has a relatively simple route of metabolism that is similar to the dietetic hexose (Burdock, G. A.; Soni, M. G.; Cabin, I. G.; Evaluation of health aspects of kojic acid in food. *Regulatory and Pharmacology* 33, 80, 2001).

The antibiotic activity of the derivatives of HMP showed that it is as ineffective as antiprotozoan agents when tested against *Trypanosoma cruzi, Tetrahymena pyriformis, Euglena gracilis* and *Astasia chattoni* (Dobias, J.; Balanova, J.; Nemec, P; Effect of kojic acid phenylosazone on *Trypanosoma cruzi Biologia* (Bratislava) 35, 203, 1980). Previous studies have reported an inhibition of bacteria from various genera by HMP, including *Aerobacter, Bacillus, Chromobacterium, Clostridium, Corynebacterium, Diplococcus, Escherichia, Gaffkya, Klebsiella, Micrococcus, Neisseria, Pasteurella, Proteus, Pseudomonas, Salmonella, Staphylococcus* and *Vibrio*. This result is very promising for the development of new derivatives with more potent antibacterial activity.

Several articles have reported on studies of subchronic toxicity, chronic toxicity and carcinogenicity of HMP in the literature (Giroir, L. E.; Kubena, L. F.; Huff, W. E.; Harvey, R. B.; Elissalde, M. H.; Witzel, D. A.; Yersin, A. G.; Ivie, G. W.; The individual and combined toxicity of HMP and aflatoxin in broiler chickens. *Poult. Sci.* 70, 1351, 1991; Giroir, L. E.; Huff, W. E.; Kubena, L. F.; Harvey, R. B.; Elissalde, M. H.; Witzel, D. A.; Yersin, A. G.; Ivie, G. W.; Toxic effects of HMP in the diet of male broilers. *Poult. Sci.* 70, 499, 1991; Fujimoto, N.; Watanabe, H.; Nakatami, T.; Roy, G.; Induction of thyroid tumours in (C57BL/6Nx C3H/N)F1 mice by oral administration of HMP *Food Chem. Toxicol.* 36, 697, 1998; Kinosita, R.; Mycotoxins in fermented food *Cancer Res.* 28, 2296, 1968; Yamato, M.; Hashigaki, K.; Ishikawa, S.; Kokubu, N.; Inoue, Y.; Tsuruo, T.; Tashiro, T.; Synthesis and antitumor activity of tropolone derivatives. *J. Med. Chem.* 28, 1026, 1985; Yamato, M.; Hashigaki, K.; Sakai, J.; Kawasaki, Y.; Tsukagoshi, S.; Tashiro, T.; Synthesis and antitumor activity of tropolone derivatives *J. Med. Chem.* 30, 117, 1987). These authors present data regarding the content of HMP quantified in various types of animals and the synergistic potential with aflatoxins that this substance has, when administered in grams of HMP per kg of food over a period of established time. There are no data in the literature describing any acute toxicity that results from a single oral dose of HMP in humans, but convulsions can occur if the HMP is injected in critical quantities (Hewitt, S. D.; Hider, R. C.; Sarpong, P.; Morris, C. J.; Blake; D. R.; Investigation of the anti-inflammatory properties of hydroxypyridinones. *Ann. Rheum. Dis.* 48, 382, 1989).

Nohyneka and co-workers (Nohyneka, G. J; Kirkland, D.; Marzin, D.; Toutain, H.; Leclerc-Ribaud, C.; Kinnai, H.; assessment of the genotoxicity and human health risk of topical use of HMP [5-hydroxy-2-(hydroxymethyl)-4H-pyran-4-one] *Food and Chemical Toxicology* 42, 93, 2004) evaluated the risk of general consumption of HMP, both through food products and skin products, and concluded that this substance, in ideal doses of consumption, does not contain toxic or genotoxic effects and, thus, does not present any risk in doses of 0.03-0.06 mg/kg/day, which eliminates the toxicity risk of this substance.

Yamato and co-workers (Yamato, M.; Hashigaki, K.; Sakai, J.; Kawasaki, Y.; Tsukagoshi, S.; Tashiro, T.; Synthesis and antitumor activity of tropolone derivatives *J. Med. Chem.* 30, 117, 1987) tested the antitumoural activity of HMP against leukemia P388 in mice, showing positive effects of antitumoural activity. Subsequently, Yamato et al. (1987) reduced the doses of HMP administered by 75% and still observed an antitumoural activity for this substance.

The effects of embriotoxicity and teratogenic of HMP in rats were studied by Choudhary and co-workers (Choudhary, D. N.; Sahay, G. R.; Singh, J. N.; Antifertility and cannibalistic properties of some mycotoxins in albino rats *J. Food Sci. Technol. (Mysore)* 31, 497, 1994). The results of this study indicated that HMP did not cause any teratogenic effect; however, data showing the mutagenic effect of this agent are not yet conclusive. The continued administration of high doses of HMP in rats resulted in the induction of thyroid adenomas. This substance directly affects the role of the thyroid, mainly inhibiting the absorption of iodine, leading to decreases in T3 and T4 and increases in TSH, increasing the stimulus of TSH in the pituitary gland. Some evidence indicates that the proliferative action caused by HMP in the thyroid is not related to the genotoxicity of the substance, according to Fujimoto and co-workers (Fujimoto, N.; Onodera, H.; Mitsumori, K. Tamura, Y.; Maruyama, S.; Ito, A.; Changes in thyroid function during development of thyroid hyperplasia induced by kojic acid in F344 rats. *Carcinogenesis* 20, 1567, 1999), but is related to the gamma-pyrone chelant potential.

There is evidence in the literature regarding the mutagenicity of HMP in bacteria, especially for bacilos, according to Manabe and co-workers (Manabe, M.; Goto, T.; Tanaka, K.; Matsuura, S.; The capabilities of the *Aspergillus flavus* group to produce aflatoxins and kojic acid. *Rep. Natl. Food Res. Inst.* 38, 115, 1981) and *Salmonella*, as per Wehner and co-workers (Wehner, F. C.; Thiel, P. G.; Van Rensburg, S. J.; Demasius, I. P. C.; Mutagenicity to *Salmonella typhimurium* of some *Aspergillus* and *Penicillium* mycotoxins. *Mutat. Res.* 58, 193, 1978). Wei and co-workers (Wei, C. I.; Huang, T. S.; Chen, J. S.; Marshall, M. R.; Chung, K. T.; Mutagenicity studies of kojic acid. *Toxicol. Lett.* 59, 213, 1991), Bjeldanes and co-workers (Bjeldanes, L. F., Chew, H. Mutagenicity of 1,2-dicarbonyl compounds: Maltol, kojic acid, diacetyl and related substances. *Mutat. Res.* 67, 367, 1979) and Bhat and co-workers (Bhat, R., Hadi, S. M. Photoinduction of strand scissions in DNA by kojic acid: Role of transition metal ions and oxygen free radical intermediates in the reaction. *Mutagenesis* 7, 119, 1992) reported that HMP, in the presence of molecular oxygen and visible light, directly influences changes in the DNA of these organisms. Degradation was increased in the presence of Fe (III), Fe (II) and Cu (II).

Cotellessa and co-workers (Cotellessa, C.; Peris, K.; Onorati, M. T.; Fargnoli, M. C.; Chimenti, S.; The use of chemical peelings in the treatment of different cutaneous hyperpigmentations. *Dermatol. Surg.* 25, 450, 1999) evaluated the effectiveness of the mixture of trichloroacetic acid, glycolic acid and HMP in a skin hyperpigmentation treatment. The authors concluded that the addition of HMP improved treatment of melasma. Similar results were also described by Lim (Lim, J. T. Treatment of melasa using kojic acid in a gel containing hydroquinone and glycolic acid. *Dermatol. Surg.* 25, 282, 1999).

Several patents describe adjustments and improvements of the properties of this metabolite (see patents JP 54-92632A, JP 56-77272A, JP 60-7961B and JP 60-9722B), as well as the incorporation of fatty acids mono or di-esters, leading to improvement in the tyrosinase inhibition activity. Similarly, patents JP 3-14508A, JP 4-145096A, JP 4-187618A and JP 5-39298A have proposed several changes to the original structure of the molecule, to obtain derivatives that inhibit tyrosinase. Both glycosylated and amino protective structures were developed to increase the skin bleaching potential of this agent (see patents JP 62-3820B, JP 64-83008A, JP 1-121205A and JP 2-028105A).

The effect of HMP on parasites has been reported only in one paper, where the metabolite was related to inhibit the activity of tyrosinases 1 and 2 in *Schistosoma mansoni* eggs, avoiding the progression of the helminth cycle (Fitzpatrick, J. M. Schistosome egg production is dependent upon the activities of two developmentally regulated tyrosinases *FASEB J.* 21, 823, 2007). However, no anti-protozoan effect of HMP was demonstrated, particularly in species of *Leishmania* or host cells.

SUMMARY OF THE INVENTION

The present invention is directed to the use of 5-hydroxy-2-hydroxymethyl-γ-pirone (HMP) as a leishmanicidal agent, by activation of the host cell, which blocks the proliferation of the protozoan (e.g. *Leishmania (Leishmania) amazonensis*), which is the etiologic agent of cutaneous leishmaniasis (CL).

In one embodiment of the present invention, HMP is used to modulate the microbicidal response of the host cell (macrophage). In another embodiment, HMP is used to increase and/or intensify the immune response of macrophages and neutrophils against cutaneous leishmaniasis. In still another embodiment, HMP is used to act in the activation mechanism of the macrophage, which eliminates the protozoan due to the activity of the molecule.

The inventors have demonstrated that HMP can be used to activate treated cells, inducing an increase on actin filament polimerization, on spreading and on membrane projections, a higher number of vacuoles and endoplasmatic reticulae and a greater superoxide production, when compared with untreated control cells.

In another embodiment according to the invention, HMP is used to prepare a medicament to treat an infection caused by *Leishmania*, wherein it acts as a leishmanicidal agent. The preparation may be in form of ointment, gel, lotion, tonic or other suitable vehicle. Preferably, the preparation is for topical use. More preferably, the HMP is distributed in carriers that make easier its dispersion and skin penetration, wherein it acts as a cutaneous leishmanicidal agent. Furthermore, HMP may be combined with at least one other molecule known in the art, which has complementary action or synergic effect, to increase its leishmanicidal properties.

According to the invention, several changes to the original structure of the HMP molecule may be proposed by those skilled in the art, i.e. the molecule of HMP may be engineered in order to modify or increase its leishmanicidal properties.

DETAILED DESCRIPTION OF THE INVENTION

Metabolite Obtention

HMP was obtained from 5 mL of a solution of spores of the *Aspergillus* fungi in 400 mL of Czapeck culture medium and 6% sucrose, sterilized at 120° C. for 15 minutes. Culture was maintained at 120 rpm in a fixed temperature of 28° C. The liquid phase was filtered and lyophilized to obtain the product. Ethanol:water (80:20) was added and consecutive extractions performed to produce a product concentrate by an evaporation process. The final product was obtained by crystallization. Purity was evaluated by CLAE and was higher than 95%.

Host Cell and Parasite Culture:

The peritoneal murine macrophage cells were cultured at 37° C. and 5% $CO_2$ in Dulbecco's modified Eagle's medium (DMEM) supplemented with 10% heat-inactivated sterile filtered fetal bovine serum (FCS), 10 mM Hepes, pH 7.3, 100 U/mL penicillin and 100 lg/mL streptomycin (all from Gibco BRL/Life Technologies, Middlesex, UK). Cells were used after 24 hours of culture.

*L. amazonensis* promastigotes were obtained from the Evandro Chagas Institute in NNN medium and maintained at 26° C. in RPMI1640 medium.

Morphological Analysis and Cellular Viability:

Firstly, morphological alterations were observed by light and fluorescence microscopy, as well as transmission and scanning electron microscopy in host cells, treated or not with 10, 20 and 50 µg/mL of HMP diluted in DMEM. Viability analyses performed by through Thiazolyl Blue (MTT) e Neutral Red (NR) assays.

Leishmanicidal Activity:

Host cells were cultivated and infected or not with *L. amazonensis*, before treating or not with HMP at the same concentrations described previously.

Results:

Results demonstrate that the secondary metabolite of HMP was able to activate cells treated, causing an increase on actin filament polymerization and spreading, as compared with control cells. Electron microscopic examination showed significant morphological changes in treated cells. Mitochondria were observed with normal morphology, increased membrane projections were seen and the cytoplasm contained a high number of vacuoles and endoplasmatic reticulae when compared with control cells. Moreover, those alterations were not due to unspecific cytotoxic effect, as observed by MTT (3-[4,5-dimethylthiazol-2-yl]-2,5-diphenyltetrazolium bromide) and NR (neutral red) assays. Furthermore, a greater superoxide production, as detected by histochemical assay with Nitro Blue Tetrazolium (NBT), was observed in infected cells with *L. amazonensis* during treatment with 50 µg/mL, when compared with control cells.

Another effect of HMP observed was the inhibition by 68% of *Leishmania promastigotes* and a 79% reduction in amastigotes during in vitro infection when cells were treated with 50 µg/mL. In addition, ultrastructural observations of the parasites inside the macrophages showed that HMP affected the intracellular amastigote, causing morphological alterations and death.

Disease control is only possible following host cell activation against the escape mechanism of the parasite. HMP, at a minimal concentration of 50 µg/mL, was demonstrated to have a leishmanicidal activity, particularly activating the host cell microbicidal response. As such, HMP holds promise as a candidate for cutaneous leishmaniasis treatment. The biotechnological aspects of its production on a large scale due to ease of substrate access, in addition to the available technology for the production of HMP and absence of collateral reactions due biochemical profiles, make this an agent worthy of study for commercial production as a leishmanicidal agent.

The invention claimed is:

1. A method of reducing proliferation of a *Leishmania* protozoan in host cells, the method comprising: exposing host cells to a leishmanicidal agent comprising: 5-hydroxy-2-hydroxymethyl-γ-pyrone (HMP).

2. The method according to claim 1, wherein HMP modulates the microbicidal response of the host cell.

3. The method according to claim 2, wherein HMP increases, intensifies, or both increases and intensifies the immune response of macrophages and neutrophils against cutaneous leishmaniasis.

4. The method according to claim 2, wherein the host cell is a macrophage and the HMP modulates the activation mechanism of the macrophage, which eliminates the protozoan due to the activity of the molecule.

5. The method according to claim 2, wherein HMP activates treated cells, inducing one or more cellular changes selected from the group consisting of: an increase on actin filament polymerization, an increase on spreading and on membrane projections, a higher number of vacuoles and endoplasmatic reticulae, and a greater superoxide production, when compared with untreated control cells.

6. The method according to claim 1, wherein the *leishmania* protozoan is *Leishmania amazonensis*.

* * * * *